(12) United States Patent
Esser

(10) Patent No.: US 11,016,080 B2
(45) Date of Patent: May 25, 2021

(54) MEDICAL DEVICE AND METHOD OPERATING SAME

(71) Applicant: Sanofi-Aventis Deutschland GMBH, Frankfurt am Main (DE)

(72) Inventor: Mario Esser, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 445 days.

(21) Appl. No.: 15/022,030

(22) PCT Filed: Sep. 19, 2014

(86) PCT No.: PCT/EP2014/070002
§ 371 (c)(1),
(2) Date: Mar. 15, 2016

(87) PCT Pub. No.: WO2015/040164
PCT Pub. Date: Mar. 26, 2015

(65) Prior Publication Data
US 2016/0231308 A1    Aug. 11, 2016

(30) Foreign Application Priority Data

Sep. 20, 2013 (EP) ..................... 13185394

(51) Int. Cl.
*G01N 33/48* (2006.01)
*G01N 33/49* (2006.01)
*G16H 10/60* (2018.01)
*G16H 40/63* (2018.01)

(52) U.S. Cl.
CPC ............. *G01N 33/49* (2013.01); *G16H 10/60* (2018.01); *G16H 40/63* (2018.01)

(58) Field of Classification Search
None
See application file for complete search history.

(56) References Cited

U.S. PATENT DOCUMENTS

| | | | |
|---|---|---|---|
| 7,570,980 B2 | 8/2009 | Ginsberg | |
| 2007/0016449 A1 | 1/2007 | Cohen et al. | |
| 2007/0158335 A1* | 7/2007 | Mansbery | F24C 7/082 219/505 |
| 2008/0255707 A1 | 10/2008 | Hebblewhite et al. | |
| 2010/0317950 A1* | 12/2010 | Galley | G06F 19/3456 600/365 |
| 2011/0077493 A1 | 3/2011 | Shadforth et al. | |
| 2011/0319322 A1* | 12/2011 | Bashan | A61B 5/14532 514/5.9 |
| 2012/0266251 A1 | 10/2012 | Birtwhistle et al. | |

(Continued)

FOREIGN PATENT DOCUMENTS

| | | |
|---|---|---|
| CN | 101272734 | 9/2008 |
| CN | 102549583 | 7/2012 |
| EP | 0688571 | 12/1995 |

(Continued)

OTHER PUBLICATIONS

International Preliminary Report on Patentability in International Application No. PCT/EP2014/074146, dated May 17, 2016, 8 pages.
International Search Report and Written Opinion in International Application No. PCT/EP2014/074146, dated Feb. 18, 2015, 14 pages.
Rote Liste, "50. Hypophysen-, Hypothalamushormone, andere regulatorische Peptide u. ihre Hemmstoffe," Chapter 50, ed. 2008, 20 pages.
International Preliminary Report on Patentability in International Application No. PCT/EP2014/070002, dated Mar. 22, 2016, 7 pages.

(Continued)

*Primary Examiner* — Anna Skibinsky
(74) *Attorney, Agent, or Firm* — Fish & Richardson P.C.

(57) ABSTRACT

The present invention refers to a medical device (100) comprising: •a measurement unit (110) adapted to measure a value of a physiological parameter, for example a blood glucose level, •a data storage (130) adapted to store ○a plurality of measurement values of the physiological parameter, ○for each measurement value an associated event tag, ○for each measurement value an associated time stamp, ○for each at least one predefined event an associated current time range for tagging preselection, •a processor (140) adapted to ○receive from the measurement unit (110) or from the data storage (130) a new measurement value with an associated time, ○comparing the associated time stamp of the new measurement value with the stored at least one time range for tagging preselection, ○if the time stamp is within one current time range for tagging preselection the corresponding tag of the predefined event is preselected and initiated for user confirmation, ○in case one particular predefined tag of one particular predefined event is then selected and confirmed with regard to the new measurement value, the associated time stamps of a predefined number of consecutive recent measurement values tagged with the one particular predefined event is received from a data storage (130), ○calculate a new time range for tagging preselection for the one predefined event at least partly based on the associated time stamps of the predefined number of consecutive recent measurement values and on the associated time stamp of the new measurement value, preferably only if at least one validation criterion is met, and ○initiate storing the new time range as current time range for tagging preselection for the one particular predefined event in the data storage (130), preferably only if the at least one validation criterion is met. The invention further refers to a corresponding method and computer program for operating a medical device as well as to a corresponding computer program product.

14 Claims, 7 Drawing Sheets

(56) References Cited

U.S. PATENT DOCUMENTS

Figure 1:
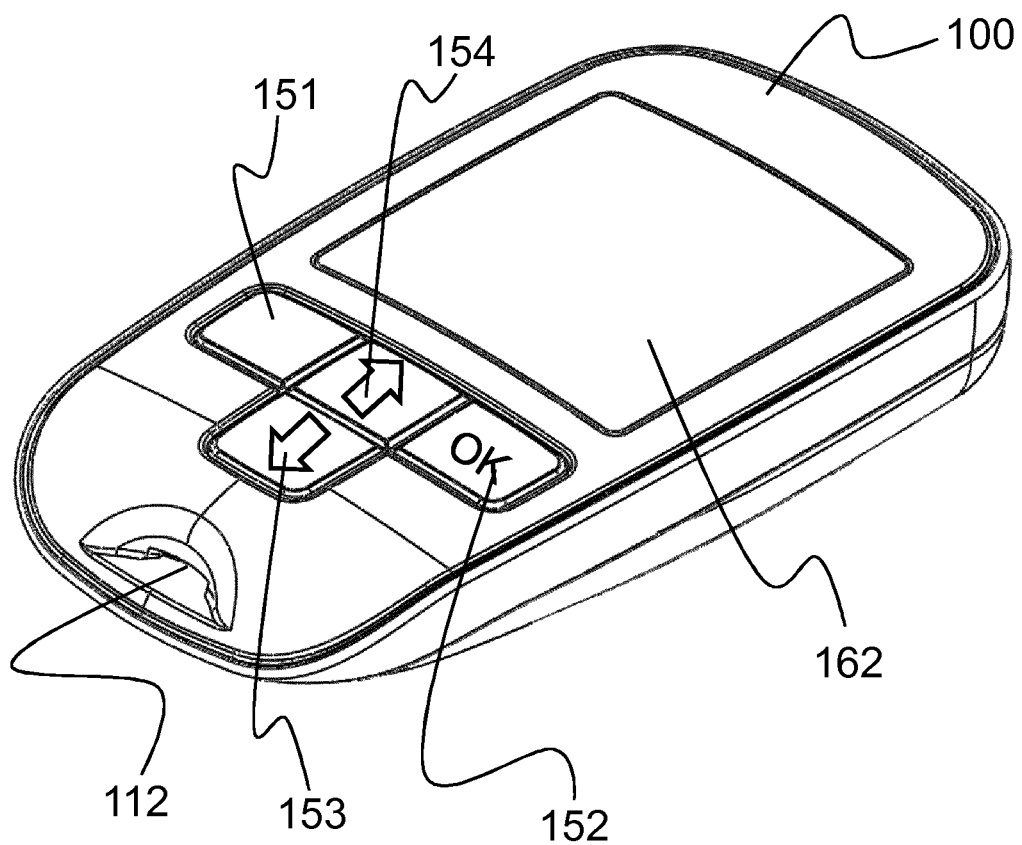

| | | | |
|---|---|---|---|
| 2013/0164718 A1* | 6/2013 | Buck | G09B 19/0092 434/127 |
| 2014/0006182 A1* | 1/2014 | Wilson | G06Q 50/12 705/15 |

FOREIGN PATENT DOCUMENTS

| | | |
|---|---|---|
| EP | 1603611 | 5/2008 |
| EP | 2085029 | 8/2009 |
| JP | 2007/510469 | 4/2007 |
| JP | 2009-500744 | 1/2009 |
| JP | 2013-505808 | 2/2013 |
| WO | WO98/56436 | 12/1998 |
| WO | WO99/38554 | 8/1999 |
| WO | WO 2005/046559 | 5/2005 |
| WO | WO 2007/005170 | 1/2007 |
| WO | WO 2011/007051 | 1/2011 |
| WO | WO2011/039163 | 4/2011 |
| WO | WO 2011/041007 | 4/2011 |

OTHER PUBLICATIONS

International Search Report and Written Opinion in International Application No. PCT/EP2014/070002, dated Dec. 3, 2014, 9 pages.

Dassau et al., "Detection of a meal using continuous glucose monitoring," Diabetes care, American Diabetes Association 31(2):295-300, Feb. 1, 2008.

* cited by examiner a)   b)   c)

MEDICAL DEVICE AND METHOD OPERATING SAME

CROSS-REFERENCE TO RELATED APPLICATIONS

This application is a U.S. national stage application under 35 USC § 371 of International Application No. PCT/EP2014/070002, filed on Sep. 19, 2014, which claims priority to European Patent Application No. 13185394.7, filed on Sep. 20, 2013, the entire contents of which are incorporated herein by reference.

The present invention relates to a medical device, preferably a glucose meter, a method for operating same, a respective computer program and a computer program product.

The following description of the invention mainly refers to diabetes as a health problem and the blood glucose level as the physiological parameter to be controlled in order to assess the effectiveness of the prescribed treatment. However, the invention may also be used with regard to other health problems and for management of other physiological parameter data like (a) blood pressure in hypertensive heart disease, (b) cholesterol or lipoprotein profile in patients with risk factors for heart disease and stroke, (c) peak flow in asthmatic patients, or (d) coagulation in patients treated for hemophilia.

Diabetes mellitus is a group of metabolic diseases in which a person has high blood sugar, either because the pancreas does not produce enough insulin, or because cells do not respond to the insulin that is produced. The treatment of diabetes concentrates on keeping blood sugar levels as close to normal ("euglycemia") as possible, without causing hypoglycemia. This can usually be accomplished with diet, exercise, and use of appropriate medications (insulin in the case of type 1 diabetes; oral medications, as well as possibly insulin, in type 2 diabetes).

Essential elements of the management of diabetes with insulin are periodic checks of the glucose concentration in the blood performed by the patients themselves, in order to obtain regular information on the progress and success of the prescribed treatment. This understanding, and patient participation is vital, since the complications of diabetes are far less common and less severe in patients who have well-managed blood sugar levels. With regard to this it has to be considered that the blood glucose level fluctuates throughout the day and is directly influenced by the amount of insulin administered, as well as lifestyle factors such as the amount and kind of food that is consumed, the exercise level and stress.

Therefore, the monitoring of the sugar level in the blood serves a dual purpose: on the one hand it provides the patient with information about the current status of glycemic control. On the other hand can the measured values serve as information for the patient or a healthcare professional (HCP) to determine whether an adjustment in the medication, namely the amount of insulin to be taken, is indicated.

In order to achieve these goals or to get as close as possible to the desired glycemic control, it is common practice that blood glucose measurement (BGM) values are monitored once or several times during the day, following a testing regime normally prescribed by an HCP.

A special role is played by the so-called fasting blood glucose measurement value (FBG). A fasting blood glucose value is derived after several hours without eating (6 to 8 hours). The fasting blood glucose measurement value is typically taken in the morning before breakfast and is the most commonly performed test among insulin treated patients as it is used to assess the quality of the titration of long-acting basal insulin or analogs such as insulin glargine.

In order to adjust or to adapt the therapy it is helpful to record the results of all blood glucose measurements and to analyze these results with a data management unit. Therefore, typically a portable monitor is used which may be able to measure the blood glucose level as well or which receives the measurement values from a blood glucose measurement device. A wireless or wired data transfer can be used to transport the results from the measurement device to the data management unit.

In addition to the mere monitoring of the blood glucose level diabetic individuals often have to maintain tight control over their lifestyle so that they are not adversely effected by, for example, irregular food consumption or exercise. Further the HCP needs detailed information on the lifestyle of the patient to provide effective treatment or modification of treatment for controlling the disease. In former times, one of the ways of monitoring the lifestyle of a patient with diabetes has been for the individual to keep a paper logbook of their lifestyle. Currently, a number of portable electronic devices exists that can measure glucose levels in an individual and store the levels for recalling and uploading to another computer for analysis. Further, they provide functionality for storing lifestyle data for example by using a tag or flag associated to the individual measurement value.

Document EP 2 085 029 A1 refers to a method of operating an analyte measurement device having a display, user interface, processor, memory and user interface buttons. After measuring an analyte with the analyte measurement device the measurement value is displayed and the user is prompted to select a flag to associate the flag with the value. By pressing only one of the user interface buttons once the flag with the value of the device is stored. In particular, the user is prompted whenever a measuring step indicates that an analyte value is outside a predetermined range.

Document U.S. Pat. No. 7,570,980 B2 discloses blood glucose measurement data stored in an array comprising associated time code information for each measurement and various other flags. These flags may correspond to specific time frames, date information, calibration check information etc. From the measured and flagged values the so called effective meal average value is calculated encompassing the measurement values that occur at specific times, for example one hour before and one hour after a specified meal time.

Document WO 2011/007051 A1 refers to a method for controlling the measurement process of the blood glucose of a patient, wherein a web application is arranged to collect measurement data from a measurement device, e.g. a blood glucose meter, and to analyze the collected data. Therein measurements are linked to events either fully manually or as pair measurements, namely pre-measurements and post-measurements, by pre-determined or adaptive time windows. For that is assumed that optimally the later measurement occurs after a fixed period of time (the time window) after the earlier measurement. A fixed period of time may be e.g. two hours plus/minus 15 minutes.

As flags or tags are effective means in order to make the life of a diabetes patient easier they are nowadays widely used for data management. However, providing one measurement value with an associated tag or flag information is sometimes difficult for the patient. Further, it is important to make sure that the correct tag information is stored with the associated measurement value because if the information is confused the additional information which is provided with the tag to the measurement value is worthless.

Hence, aspects of the invention may include a medical device and the respective method which adapts tagging to the user's habits and makes it easier to tag the data correctly.

The above problem is solved by a medical device with the features of claim 1.

In particular the inventive medical device comprising
a measurement unit adapted to measure a value of a physiological parameter, for example a blood glucose level,
a data storage adapted to store
 a plurality of measurement values of the physiological parameter,
 for each measurement value an associated event tag,
 for each measurement value an associated time stamp,
 for each at least one predefined event an associated current time range for tagging preselection,
a processor adapted to
 receive from the measurement unit or from the data storage a new measurement value with an associated time stamp,
 comparing the associated time stamp of the new measurement value with the stored at least one time range for tagging preselection,
 if the time stamp is within one current time range for tagging preselection the corresponding tag of the predefined event is preselected and initiated for user confirmation,
 in case one particular predefined tag of one particular predefined event is then selected and confirmed with regard to the new measurement value, the associated time stamps of a predefined number of consecutive recent measurement values tagged with the one particular predefined event (i.e. the corresponding tag of the one particular predefined event was confirmed for these measurement values and stored in the data storage) is received from a data storage,
 calculate a new time range for tagging preselection for the one predefined event at least partly based on the associated time stamps of the predefined number of consecutive recent measurement values and on the associated time stamp of the new measurement value, preferably only if at least one validation criterion is met, and
 initiate storing the new time range as current time range for tagging preselection for the one particular predefined event in the data storage, preferably only if the at least one validation criterion is met.

The time stamp associated to each measurement value comprises date and time information of a certain time point during the measurement process resulting in the respective measurement value, for example the completion of the measurement process.

With the event tag additional information associated with the measurement value is provided as explained above. Preferably, the event tag for blood glucose measurement values comprises the event nil (no-tag) and in particular at least one of the following group of events comprising fasting, pre-meal, post-meal, pre-meal breakfast, post-meal breakfast, pre-meal lunch, post-meal lunch, pre-meal supper, post-meal supper, night time and exercise.

The time range for tagging preselection for the at least one predefined event refers to a time range which is used to support the user during tagging as follows. After finishing the measurement of a new value of the physiological parameter the time information of the associated time stamp is compared with the time range for tagging preselection. If the time information lies within the time range, the corresponding tag of the predefined event is preselected and provided at the display for user confirmation. For example, if the current time range for the fasting blood glucose tag comprises the range between 6 a.m. and 8 a.m. than for each measurement value measured within this time range the fasting tag is preselected (preferably if no other measurement value of that day comprises the fasting tag) and may be confirmed by the user afterwards as described below in detail.

If, for example by a change in the habits of the user/patient now measures its fasting blood glucose value later than e.g. 8 a.m. the time range for fasting tag preselection is automatically changed. This is realized by considering the associated time stamps of a predefined number of consecutive recent measurement values tagged with the event, e.g. the fasting event, and the associated time stamp of the new measurement value. A new time range is calculated based on the time stamps of at least a part of the consecutive recent measurement values and on the associated time stamp of the new measurement value. After recalculation (shift) according to the changed habit the storage of the new, shifted time range as current time range for tagging preselection of the associated predefined event in the data storage is initiated. The previous time range may be deleted or overwritten.

Hence, the inventive medical device allows to adapt the preselected tag to the user's habits. It further makes it easier for the user to choose the correct tag with the measurement value.

In an embodiment at least one validation criterion is considered for the steps of calculation a new time range and/or storage of the new time range. For example as one validation criterion it is determined whether the associated time stamps of the predefined number of consecutive recent measurements tagged with the one particular predefined event and the associated time stamp of the new measurement value for the one particular predefined event are outside the current time range in the same direction. Only if the validation criterion is met, i.e. if either all time stamps of the predefined number of consecutive recent measurement values and the time stamp of the new measurement value lie before or if all time stamps (of the predefined number of measurement values and of the new measurement value) lie after the current time range, the processor executes the step of calculation the new time range for tagging preselection and/or the step of initiation of storing the new time range for tagging preselection.

Considering the above validation criterion has the advantage that a too frequent (unintended) change of the time range for tagging preselection is avoided. Only in cases in which the current time range for tagging preselection does not fit at all to the changed habits of the user/patient the time range for tagging preselection is changed.

In an embodiment the time range for tagging preselection of a certain event may be different for working days and non-working days. In this case the determination whether the associated time stamps of a predefined number of consecutive recent measurement values tagged with the event are outside the associated current time range comprises not only the time information of the time stamp but also the date information. Preferably, in this case the time stamps of consecutive recent measurement values compared with the current time range either only refer to working days or non-working days according to the time stamp of the new measurement.

The above problem is also solved by a system comprising the above mentioned medical device and a case adapted to carry and secure the medical device and preferably a box containing test strips and/or a lancet. The case further comprises additionally at least one flash card containing information related to the use of the device, preferably with regard to the different trend categories or tags as well as to the operation of the medical device. In an embodiment the at least one flash card is fixed by two rings or a hinge to the case so that an easy access is provided for the user/patient to the information contained at the backside of such a flash card by hinging down the respective card. In this position the card is still fixed to the case and therefore cannot get lost.

For the same reason the above problem is also solved by a method for operating a medical device with a data storage comprising for at least one predefined event an associated current time range for tagging preselection, wherein the method comprises the following steps:

receiving from a measurement unit or from the data storage a new measurement value of a physiological parameter, for example the blood glucose level, with an associated time stamp comparing the associated time stamp of the new measurement value with the at least one current time range for tagging preselection, preselecting the corresponding tag of the predefined event and initiating display of the corresponding tag for user confirmation if the time stamp of the new measurement is within one current time range for tagging preselection, in case one particular predefined tag of one particular predefined event is then selected and confirmed with regard to the new measurement value, receiving from a data storage the associated time stamps of a predefined number of consecutive recent measurement values tagged with the one particular predefined event, calculating a new time range for tagging preselection for the one particular predefined event at least partly based on the associated time stamps of the predefined number of consecutive recent measurement values and on the associated time stamp of the new measurement value, preferably only if at least one validation criterion is met, and storing the new time range as current time range for tagging preselection for the one particular predefined event in the data storage, preferably only if the at least one validation criterion is met.

Analogous to the inventive medical device the validation criterion of the inventive method comprises the step of determining whether the associated time stamps of the predefined number of consecutive recent measurement values and the associated time stamp of the new measurement value are outside the current time range for tagging preselection for the one particular predefined event in the same direction.

In an embodiment of the inventive medical device or method the predefined number of consecutive measurement values (preferably including the new measurement value) is 2 or greater, preferably 4 or greater, resulting in at least 3 to 5 time stamps, respectively, for the calculation including the associated time stamp of the new measurement value. Already this small number of recent consecutive measurement values may reveal a habit change.

In another embodiment of the inventive medical device or method the time range for tagging preselection of the at least one event is defined by a center time and a duration, wherein the shift of the time range is calculated in an easy and effective way as shift of the center time corresponding to the average value of the time stamps of the at least one part of the predefined number of recent consecutive recent measurement values, preferable as an average value of the time stamps of all of the predefined number of consecutive recent measurement values, wherein the duration of the time range is not changed.

In an exemplary embodiment the average value is the arithmetic mean value or the median value of a time information of the time stamps (without considering the date).

For the same reason as explained above the problem is solved by a computer program for operating a medical device with a data storage comprising for each at least one predefined event an associated current time range for tagging preselection, the computer program comprising:

code for receiving from a measurement unit or from the data storage of a new measurement value of a physiological parameter, for example a blood glucose level, with an associated time stamp, code for comparing the associated time stamp of the new measurement value with the at least one current time range for tagging preselection, code for preselecting the corresponding tag of the predefined event and initiating display of the corresponding tag for user confirmation if the time stamp of the new measurement is within one current time range for tagging preselection, code for receiving from a data storage the associated time stamps of a predefined number of consecutive recent measurement values tagged with one particular predefined event in case the corresponding predefined tag of the one particular predefined event is then selected and confirmed with regard to the new measurement value, code for calculating a new time range for tagging preselection for the one particular predefined event at least partly based on the associated time stamps of the predefined number of consecutive recent measurement values and on the associated time stamp of the new measurement value, preferably only if at least one validation criterion is met, and code for storing of the new time range as current time range for tagging preselection for the one particular predefined event in the data storage, preferably only if the at least one validation criterion is met.

The above computer program may be realized with the embodiments as mentioned above with regard to the above inventive method for operating a medical device.

The above problem is further solved by computer program product comprising a computer-readable medium bearing computer program code embodied therein for use with a computer, wherein the computer program code comprises the above mentioned computer program.

The invention not only refers to a time range for fasting tag preselection but may be also adapted analogously to other tags/flags.

The above-mentioned advantages as well as other advantages of various aspects of the present invention will become apparent to those of ordinary skill in the art by reading the following detailed description with the explanation of the accompanying drawings. All features described above and below and/or illustrated per se or in any combination form the subject-matter of the invention, independent of their inclusion in the claims or their back-reference.

Figure 2:
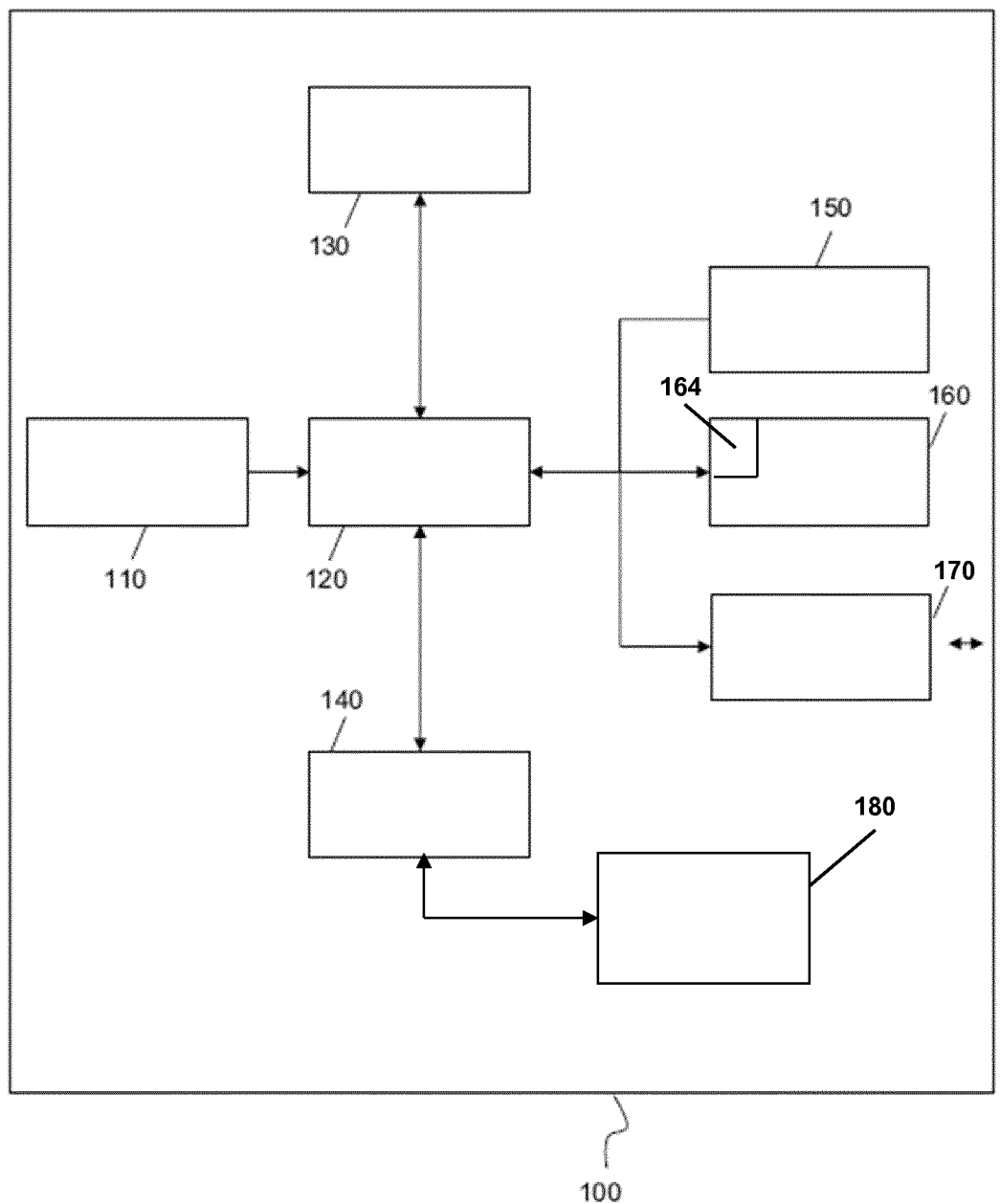
Figure 3:
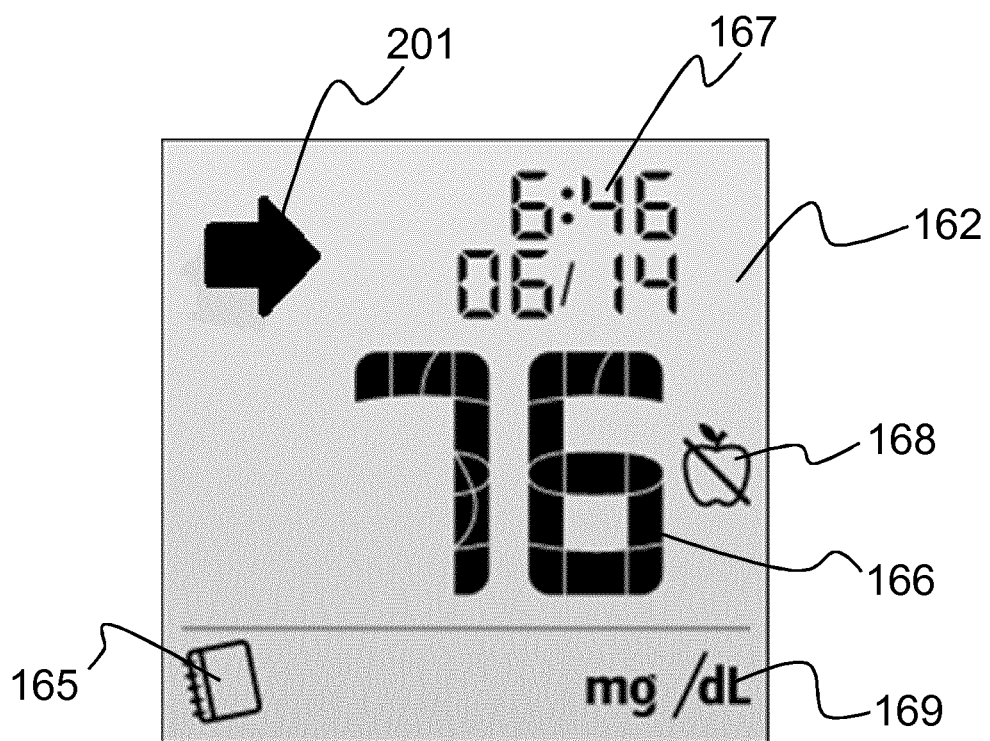
Figure 4:
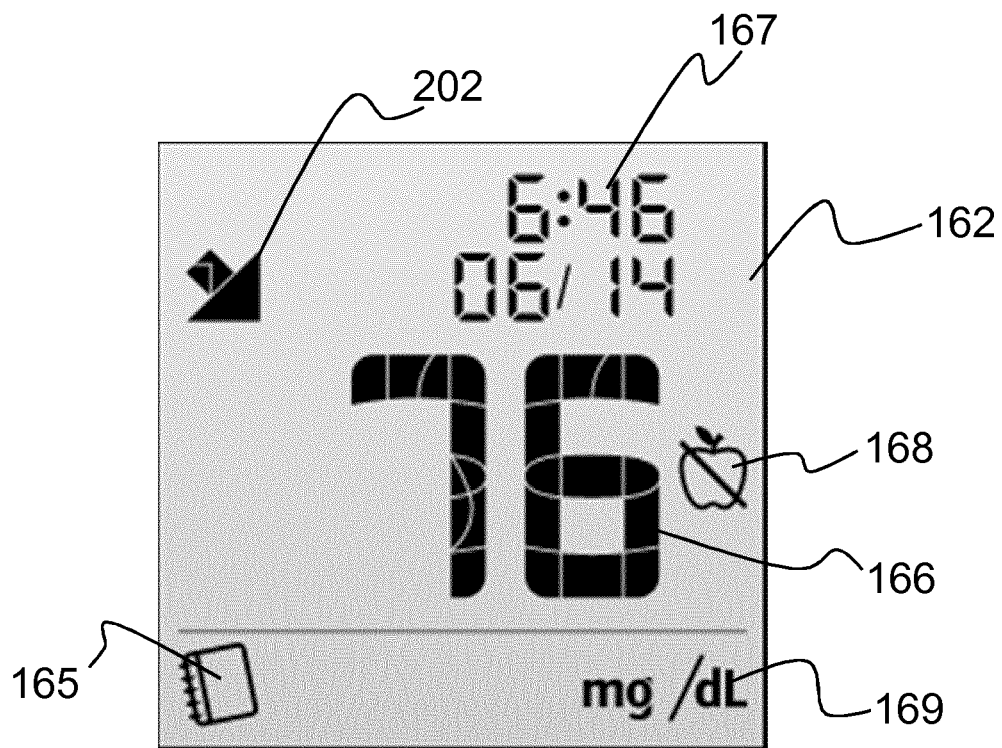
Figure 5:
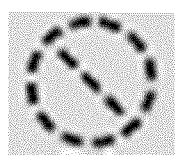
Figure 5:
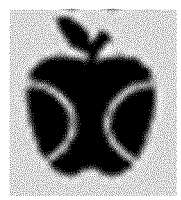
Figure 5:
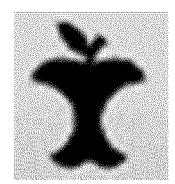
Figure 6:
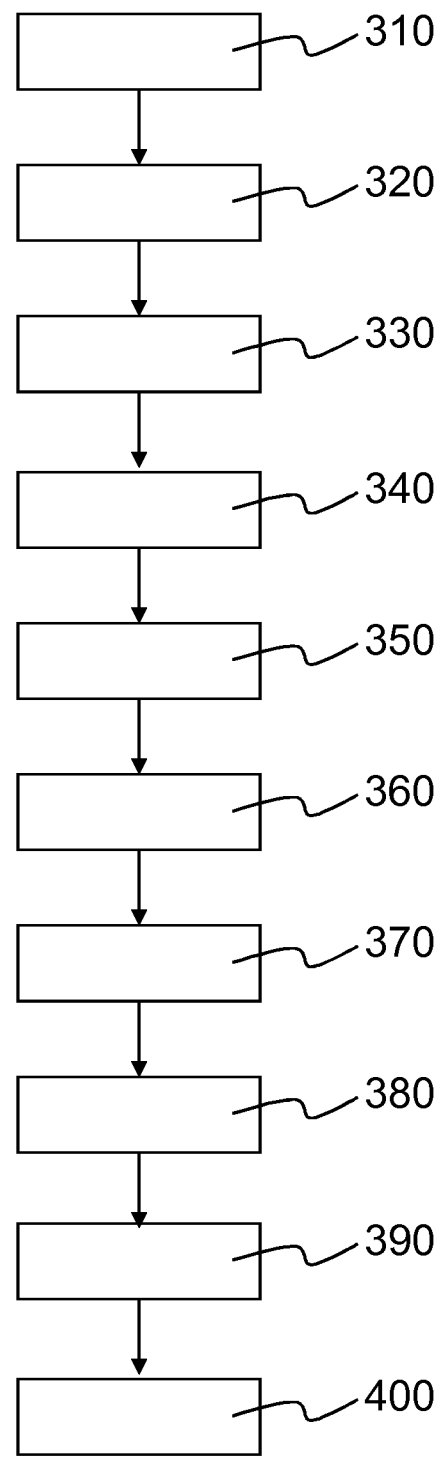
Figure 7:
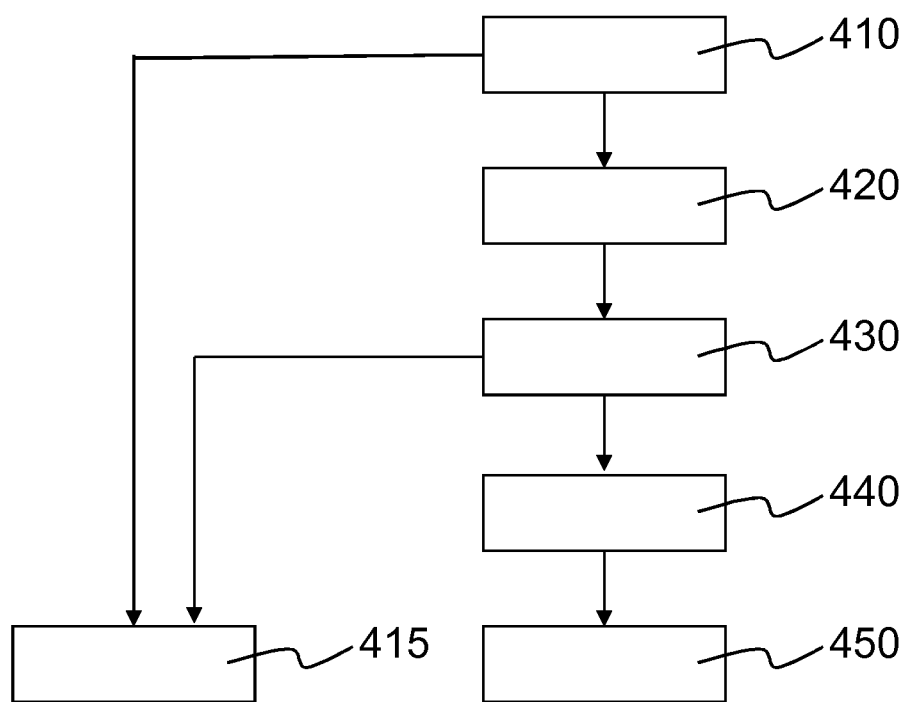
Figure 8:

Exemplary embodiments of the present invention are described herein with reference to schematic drawings, in which FIG. 1 shows the medical device according to a preferred embodiment of the invention in a perspective view;

FIG. 2 shows a diagram of the medical device as shown in FIG. 1;

FIG. 3 a first example of the display of the medical device as shown in FIG. 1 in a "Logbook" mode;

FIG. 4 a second example of the display of the medical device as shown in FIG. 1 in a "Logbook" mode;

FIG. 5 further examples of tag signs as they are displayed on a display of the medical device as shown in FIG. 1;

FIG. 6 a flow diagram containing a procedure realized by the inventive medical device in the "Measure BG" mode;

FIG. 7 another flow diagram comprising an embodiment of the inventive method for indicating a trend; and FIG. 8 an inventive system comprising a case and the medical device according to FIG. 1 in a top view, wherein the case is in an open state.

The following paragraphs will describe various embodiments of the invention. For exemplary purpose only, the embodiments are outlined in relation to a medical device supporting health control and the trend indication method with regard to blood glucose level measurement, in particular with regard to fasting blood glucose level measurement. However, the used terminology and the description of the embodiments with respect to the medical device or health indicating method are not intended to limit the principles and ideas of the invention to such a single device or method and may be adapted to other physiological values accordingly.

FIG. 1 is a schematic drawing and FIG. 2 is a schematic diagram of the medical device 100 according to a preferred embodiment of the invention. Preferably, the medical device 100 comprises a blood glucose measurement unit 110, which is arranged to measure the blood glucose level. Further, the measurement unit 110 comprises an interface and a slot 112 for inserting a test strip.

The blood glucose measurement unit 110 is connected to a receiving unit 120, which is arranged to forward e.g. blood glucose measurement data received from blood glucose measurement unit 110 to a data storage 130 (storage unit or means) or memory, such as a Flash memory. Alternatively, the receiving unit 120 may retrieve stored data such as e.g. blood glucose value data from the storage 130 and forward it to a processor 140 (processing unit or means), such as a microcontroller or microprocessor, a digital signal processor, and/or the like. Alternatively, the receiving unit 120 directly forwards the blood glucose value data received from the blood glucose measurement unit 110 to the processor 140.

Receiving unit 120 is further connected to a user input unit 150 of a user interface. The user input unit 150 is arranged to receive input from the user of the medical device 100 for example by key 151, confirmation key (OK button) 152, key 153 for scrolling down (downward button) and key 154 for scrolling up (upward button). The user input data are forwarded from the user input unit 150 to the receiving unit 120, which either forwards it to the processor 140 or to the data storage 130.

Furthermore, the user interface of medical device 100 comprises a display unit 160 with a display 162, which is connected to the receiving unit 120 as well. Preferably, the display unit 160 receives data to be displayed by the display 162 from the receiving unit 120 or the processor 140.

Preferably, the medical device 100 additionally comprises a further interface 170, for example a wired interface such as a serial port, a Universal Serial Bus (USB) interface, a mini-USB interface, or a wireless interface such as an infrared (e.g. an IRDA) interface, a Bluetooth™ interface, and/or the like, in order to receive data and/or to transmit data. The interface 170 is preferably connected to the receiving unit 120 in order to receive data from the receiving unit 120 and/or to forward data to the receiving unit 120.

Additionally, the medical device 100 comprises a clock unit 180 which provides a date and time information, preferably based on a clock generator, which may be displayed at the display 162. Further, the clock unit 180 provides date and time information in particular for generating a time stamp for an associated blood glucose measurement.

As outlined above, the medical device 100 preferably comprises a blood glucose measurement unit 110. Preferably, the blood glucose measurement unit 110 is arranged to measure the blood glucose level in the blood of e.g. the user by testing a drop of blood on a test strip that is inserted into the slot 112. The measurement may be made by e.g. an electrochemical method or an optical method. Full insertion of the test strip in the slot 112 may be detected by a respective sensor. The measured blood glucose value is transformed to blood glucose value data and forwarded preferably immediately or on demand to the receiving unit 120. Alternatively, the blood glucose measurement unit 110 is arranged to measure the blood glucose level of the user via infrared diagnosis or an alternative contactless measurement method.

According to a further alternative (not depicted in FIG. 1) the blood glucose measurement unit 110 is implanted in the body of the user of the medical device and forwards the data to the receiving unit 120 either via a wired connection or via a wireless connection. In an embodiment, such an implanted blood glucose measurement unit 110 is a continuous measurement sensor e.g. based on a chip which may allow a continuous closed loop control. In the latter case the medical device comprises two parts, one part contains the measurement unit 110 and the other part the remaining units of the medical device. The blood glucose measurement unit 110 preferably forwards the blood glucose measurement value data to the receiving unit 120 via interface 170. According to a further alternative the medical device does not comprise a blood glucose measurement unit which measures the blood glucose values, but receives blood glucose value data from an external unit.

The measurement of the blood glucose measurement is preferably triggered by the receiving unit 120 which sends a respective signal to the blood glucose measurement unit 110. According to one preferred alternative the receiving unit 120 receives a trigger signal generated by user input which is received via user input unit 150 or based on a signal from the slot 112 detecting a test strip. Alternatively, the trigger signal is generated automatically by the clock unit 180 or by the processor 140.

Preferably, the receiving unit 120 is represented e.g. by the input ports and output ports of a microprocessor or a bus system managing the data handling between several functional units. This includes bus systems, such as e.g. Advanced Microprocessor Bus Architecture bus systems implemented in a microprocessor or external bus systems connected to a microprocessor. Via the receiving unit 120, data are retrieved from the data storage 130 on demand and forwarded to the processor 140, to the display unit 160 or to the interface 170. Moreover, the receiving unit 120 forwards control signals, such as trigger signals or control signals e.g. to the blood glucose measurement unit 110, the display unit 160 or the interface 170.

The data storage 130 is arranged to store data entered via the user input unit 150, a plurality of blood glucose measurement data received from the blood glucose measurement unit 110 together with the time stamp and/or at least one event tag associated to each measurement data, data calculated from the plurality of blood glucose measurement values processed by the processor 140 and/or data received via interface 170.

Further the data storage 130 stores parameter data like an associated time range for tagging preselection regarding for example a fasting tag, a pre-meal tag or a post meal tag. Preferably such a time range is defined using a center time and a duration, wherein the time range comprises the time around the center time with the size of ½ duration in both directions. For example, the time range for fasting tagging preselection is defined with a duration of 2 hours and a center time at 7 a.m., so that the time range for fasting tagging preselection encompasses the time between 6 a.m. and 8 a.m.

Additionally, for example the data storage 130 stores the following preset time ranges for pre- and post-meal times, preferably for tagging preselection:
pre-meal breakfast: 5:00 a.m. to 8:59 a.m.
post-meal breakfast: 9:00 a.m. to 10:59 a.m.
pre-meal lunch: 11:00 a.m. to 11:59 a.m.
post-meal lunch: 12:00 p.m. to 3:59 p.m.
pre-meal supper: 4:00 p.m. to 6:59 p.m.
post-meal supper: 7:00 p.m. to 8:59 p.m.
night time or bedtime: 9:00 p.m. to 11:59 p.m.

Mealtime and fasting time ranges may be settable by the user "Settings" mode of the medical device.

Furthermore, data storage 130 is arranged to provide the stored data to the processor 140, to the display unit 160 and/or to the interface 170. The data storage 130 is preferably implemented as a semiconductor memory such as a Flash memory. Alternatively, it is implemented as a hard disk memory or an on-chip memory of the processor 140.

The processor 140 is preferably a microprocessor or any other functional unit capable of processing data.

The user input unit 150 is preferably implemented as a keyboard comprising one or more push buttons 151, 152, 153, 154. The keyboard may comprise one or more soft keys, wherein the function of the soft keys may be displayed on the display 162. Alternatively, the user input unit 150 is a key board or a touch screen. Alternatively, the user input unit 150 comprises a microphone for receiving speech input so that data can be entered via speech input.

After a blood glucose measurement a tag may be associated to the measurement value referring to lifestyle data by pressing the up or down keys 153, 154 scrolling upwards or downwards through the different tags which are for example the fasting tag, pre-meal tag, post-meal tag and no-tag respectively referring to a measurement value which is a fasting blood glucose value, a pre-meal blood glucose value, a post-meal blood glucose value and a blood glucose value that cannot be associated to one of the previous lifestyle parameter.

The display unit 160 preferably comprises an LCD or LED display 162. Preferably, the display displays a number of alphanumerical characters so that e.g. the presently measured blood glucose value can be displayed together with additional instructions for the user. Alternatively or additionally, the display unit 160 comprises a graphic display in order to display graphs or graphics such as icons. Further the display of the display unit 160 may comprise a touchscreen.

The display unit 160 further may also show a trend indicator 164 (trend indicating unit or means) which is adapted to indicate different trend categories, for example an increasing trend, a steady trend and a decreasing trend, symbolized e.g. as an arrow pointing up, an horizontal arrow 201 and an arrow pointing down 202, respectively, at the display 162 (see FIGS. 3 and 4). Alternatively or additionally, the trend may be communicated by a loud speaker, wherein the increasing trend may be represented by a tone with an increasing pitch, the steady trend by a tone with a constant pitch and the decreasing trend by a tone with a decreasing pitch.

The interface 170 is preferably a wireless interface, such as IRDA, Bluetooth™, GSM, UMTS, ZigBee, or WI-FI, etc. Alternatively, the interface is a wired interface, such as a USB port, mini-USB port, serial data port, parallel data port, etc., for receiving and transmitting data. In a further alternative embodiment the medical device 100 does not comprise an interface 170.

According to another alternative embodiment, medical device 100 comprises a memory card reader or a memory card reader interface. The memory card reader is preferably adapted to read information from a memory card, such as a Flash memory card, or any type of SIM card. For this purpose, the memory card comprises a memory, wherein at least one of a selected algorithms together with corresponding parameters, a history of the blood glucose values and/or insulin doses administered, etc. is stored. Thus, in the case that the medical device 100 has a defect, the relevant data may still be stored on the memory card which can be easily removed from the memory card reader of the medical device 100 and transferred to a new medical device 100. Moreover, the memory card 100 may be used in order to provide information on the history of the treatment to e.g. an HCP.

In the case that the memory card is a SIM card providing subscriber identification for a mobile communication network and the interface unit 170 is additionally a mobile communication interface, additional functions of the medical device 100 can be unlocked by the provider of the SIM card via a telecommunication channel. This offers the possibility that the medical device 100 can communicate with other telecommunication devices via predefined channels, such as UMTS or GSM. Via the international mobile subscriber identity, also called IMSI, stored in the SIM card, the medical device 100 identifies itself within the network and, thus, can be addressed via the network. In such a case the medical device 100 can be easily checked, remote controlled, updated, monitored, etc., via interface unit 170, e.g. by addressing the mobile communication unit with a phone number.

Furthermore, the medical device 100 is able to transmit data via SMS, e-mail or via mobile internet connection. Moreover, this offers the possibility to locate the medical device 100 in an emergency case.

In the case that the blood glucose measurement unit 110 is a continuous sensor which is e.g. implanted a dose delivery unit with an insulin pump forming an automatic delivery system may be additionally provided.

As shown in FIG. 6, the medical device 100 is capable to perform a number of operating processes. According to a preferred alternative after switching on, e.g. by pressing a key 151, 152, 153 or 154, preferably the confirmation key 152 for a predetermined time, or detection of a test strip within the slot 112, the medical device 100 performs initialization step 310 for initializing the functional components of the medical device 100. After this, the different operation modes which are implemented in the medical device 100, are displayed in the display step 320, preferably operation modes such as "Measure BG", "Logbook" and/or "Settings".

In step 330 the user selects one of the displayed operation modes via the user input unit 150, for example by means of the keys 153, 154 for scrolling down or up, and confirms the selection using the confirmation key 152.

In step 340 the selected operation mode is executed. As an example the mode "Measure BG" is selected for executing a blood glucose measurement. Upon execution of this mode the user/patient is requested to provide a test strip with a blood sample.

In the "Logbook" mode the history of previous measurements and statistical results may be calculated and displayed. The "Settings" mode allows the user to define and change some parameters of the medical device 100.

After selecting the mode "Measure BG", in step 350 a drop of blood is applied to the test portion of the test strip which is inserted in slot 112 of the medical device 100.

According to an alternative version of the operation process steps 310 to 340 may be skipped in the case that a specific operation mode is preselected. In this case, after initialization, the preselected operation mode, which is either preselected by the user or automatically selected in accordance with a specific event, for example the detection of a fully inserted test strip in slot 112, the operating process proceeds with the following step 350 and asks the user to apply a drop of blood. In step 360 it executes the preselected one or more operation modes, for example the mode "Measure BG".

Now in step 360 the measurement unit 110 determines e.g. by an electrochemical method the blood glucose level and displays the respective new measurement value at the display 162. In the next step 370 the clock unit 180 generates the time stamp of the present measurement comprising a date and time information. The time stamp is also displayed in display 162 and both, the present blood glucose measurement value and the associated time stamp is transferred by receiving unit 120 to the data storage 130.

In the next step 380 the processor 140 compares the time stamp of the present blood glucose measurement value with each of the time ranges for tagging preselection of the events stored in the data storage 130 which events may be selected as the associated event tag. If the time stamp of the present measurement value (new measurement value), in particular the time information of the time stamp, lies within the current time range of e.g. the fasting event automatically the fasting tag is provided for confirmation by the user and displayed with a respective sign 168, for example a struck out, empty apple, at display 162. In order to show that a confirmation is necessary the tag sign 168 displayed on display 162 is blinking/flashing. Now, the user may confirm the fasting tag for example by pressing the confirmation key 152. Alternatively, the user may change the tag using the up and down keys 153, 154 into the pre-meal tag, the post-meal tag or the no-tag (nil). If the correct tag is chosen the user confirms the tag by pressing the confirmation key 152. By confirmation of the tag with the confirmation key 152 the flashing of the displayed tag sign is stopped and the tag sign is displayed continuously without blinking. In this state, pressing the up/down keys 153, 154 will not change the tag. Then, the processor 140 initiates storage of the associated, confirmed tag with regard to the recent measurement value in the data storage 130 via receiving unit 120.

If in step 380 the processor 140 cannot find any range for tagging pre-selection which refers to the time information of the time stamp of the present measurement value, the no-tag is preselected.

After pressing the confirmation key 152, if the user presses the confirmation key again, the tag will start flashing again and pressing the up/down key will again allow the user to change the tag as explained above.

Further, in the "Logbook" mode the user is allowed to change the tag in the above explained manner but only within a predefined time range from the associated time stamp of the blood glucose measurement value, for example within 10 days.

If the time stamp of the recent measurement value falls within the current time range for tagging pre-selection and there is already a measurement value in that day marked as fasting the fasting tag is not automatically displayed and not selectable and therefore may not be associated to the recent measurement value.

Further, if, for example the fasting time range for tagging preselection overlaps with, for example the time range for pre-meal breakfast, the fasting tag has priority over the pre-meal tag. Hence, in this case, if no fasting value is recorded for that day, the fasting tag is automatically preselected if the time stamp of the present measurement value lies within the time range for the fasting tag and the time range for pre-meal breakfast.

In another embodiment a flashing tag may not only be confirmed by the user by pressing the confirmation key 152 but also by removal of the strip from the port 112 after a blood glucose test, or when the medical device goes into sleep mode.

In the next optional step 390 a comment to the present measurement value may be selected by the user using the up and down keys 153, 154. The comment may then be confirmed with the confirmation key 152, wherein the chosen comment is then stored in the data storage 130 associated to the present measurement value as well.

In step 400 after each measurement (and finishing tagging in step 380) the processor 140 compares whether the time information of the time stamp of the last e.g. three consecutive measurement values tagged with the same event tag, for example with the fasting tag, including, if applicable, the present measurement value are outside the current time range for tagging pre-selection of the fasting event in the same direction. If not all three associated time stamps are outside the current time range in the same direction the current time range for tagging preselection of the fasting tag stored in the data storage 130 is not changed. If the processor 140 detects that all three time stamps of the three consecutive previous measurement values tagged with the fasting tag are outside the current time range in the same direction (i.e. all three time stamps exceeds the time range above or all three below) the time range is shifted. Therefore, for example the arithmetic mean value of the time information of the three time stamps is calculated and used as the new center time for the time range for tagging pre-selection of the fasting tag. The duration of the time range may stay the same.

For example, the time information of the time stamps of the recent 3 measurement values comprising the fasting tag are 8:10 a.m., 8:27 a.m. and 8:23 a.m. and the present time range for fasting tag preselection refers to a center time at 7 a.m. and a duration of 2 hours. Then, in step 400 the processor 140 determines that all time information is outside the current time range for fasting tag preselection in the same direction. In this case the time range for fasting tagging preselection is changed to a center time at 8:20 a.m. which is the arithmetic mean value of the three time stamps. This new current time range center value is then stored in the data storage 130. Hence, the time range now is between 7:20 a.m. and 9:20 a.m., as the duration is not changed, so that if the user now measures a blood glucose value within this time range automatically the fasting tag sign is displayed after finishing measurement for user confirmation.

The above explained method to adjust the time range for fasting tag preselection provides a comfortable way to cope with the user's/patient's needs and to ease the tagging procedure. Hence, correct tagging is supported by the above procedure.

The above explained adjustment may be analogously used with other tags and respective time ranges as well.

When the medical device 100 is in the "Measure BG" mode, the device may turn into the sleep state automatically after for example 120 seconds without any new action. Once the device has returned a new measurement value, the device turns to the sleep state automatically after for example 60 seconds without any user interaction.

As explained above the medical device 100 provides at least one memory review mode which is called "Logbook" mode. The respective display and calculations are explained in the following.

The "Logbook" mode is entered when the user activates the medical device 100 by pressing e.g. the confirmation button 152. Then a display as depicted in FIGS. 3 and 4 is shown.

In the "Logbook" the measurement values are preferably displayed in the order in which the entries are entered into the device, or alternatively according to the time and date assigned to the measurement values. In particular the most recent blood glucose measurement value is shown upon entry into the "Logbook" mode. Pressing the up and down keys 153, 154 the user may scroll through the records, for example by pressing the down key 153 the user may scroll backwards in time and by pressing the up key 154 the user scrolls forward in time.

Examples of a display 162 showing a measurement value are shown in FIGS. 3 and 4. The user knows from the "Book" sign 165 in the lower left corner of the display that he/she has entered the "Logbook" mode.

The display 162 in the "Logbook" mode further shows the blood glucose measurement value 166 as biggest number in the center of the screen. Above the measurement value 166 the associated time stamp 167 including date and time is displayed. On the right side the associated tag as a sign 168 is provided, wherein the sign may show for example an empty, struck out apple as shown in FIGS. 3 and 4 in case of an associated fasting tag, a full apple as shown in FIG. 5b) in case of an associated pre-meal tag, a bitten apple as shown in FIG. 5c) in case of an associated post-meal tag or a struck out circle as shown in FIG. 5a) in case of an associated no-tag. Additionally, in the lower right corner of the display 162 the measurement unit 169 for the blood glucose value is provided.

The upper left corner of the display 162 in the "Logbook" mode shows a sign representing a trend for fasting blood glucose values controlled by the trend indicator 164 which is activated in the "Logbook" mode. The trend indicator 164 shows the trend of the respective fasting blood glucose measurement value using an arrow pointing up, an arrow pointing horizontally 201 (see FIG. 3) or an arrow pointing down 202 (see FIG. 4).

The operating process of the medical device 100 for trend indication is explained in the following and is depicted in FIG. 7.

For each fasting measurement value the processor 140 selects in step 410 via the receiving unit 120 from the data storage 130 a second group of measurement values containing the fasting tag of the recent e.g. three days, for example the fasting measurement values of the present day and the two days before (days 0, −1 and −2), wherein at least two fasting measurement values within the three day period must be available. If less than two fasting measurement values, i.e. only one fasting measurement value, within the three day period is available the procedure moves to step 415 and the trend indicator 164 does not calculate and display a respective trend arrow and the display 162 stays empty in the upper left corner or shows an error sign.

Then, in step 420 the arithmetic mean value is determined from these 3 or 2 fasting measurement values as the second mean value CURR_FAST_AVG.

Further in step 430, the processor 140 selects from the data storage 130 via the receiving unit 120 a first group of measurement values based on the associated time stamp comprising seven days before the recent three days, i.e. three days to nine days prior the recent fasting measurement value (days −3 to −9), wherein at least a first number limit of for example 5 fasting measurement values within the seven day period must be available. Otherwise, the procedure moves to step 415 and the processor 140 does not calculate a trend and the trend indicator 164 does not display any trend arrow or shows an error sign.

In step 440, if there are enough fasting measurement values, from the fasting measurement values of the first group the median is determined as a first mean value PAST_FAST_MED.

Now, in the next step 450 the trend is calculated and displayed using respective arrows in the following way.

If the second mean value CURR_FAST_AVG is greater than a low limit of 125 mg/dl and the difference between the second mean value and the first mean value is greater than 20% of the second mean value (corresponding to a relative tolerance range), i.e.

(CURR_FAST_AVG−PAST_FAST_MED)>
(CURR_FAST_AVG*20%), the fasting trend up arrow is displayed on the display 162.

Also, the fasting trend up arrow is displayed on the display 162 if the second mean value CURR_FAST_AVG is less than or equal the low limit of 125 mg/dl and the difference between the second mean value and the first mean value is greater than 25 mg/dl (corresponding to an absolute tolerance range), i.e.

(CURR_FAST_AVG−PAST_FAST_MED)>25 mg/dl.

If the second mean value CURR_FAST_AVG is greater than the low limit 125 mg/dl and the difference between the first mean value and the second mean value is greater than 20% of the second mean value (corresponding to the relative tolerance range), i.e.

(PAST_FAST_MED−CURR_FAST_AVG)>
(CURR_FAST_AVG*20%), the fasting trend down arrow 202 is displayed on the display 162.

Also, the fasting trend down arrow 202 is displayed on the display 162 if the second mean value CURR_FAST_AVG is less than or equal the low limit of 125 mg/dl and the difference between the first mean value and the second mean value is greater than 25 mg/dl (corresponding to an absolute tolerance range), i.e.

(PAST_FAST_MED−CURR_FAST_AVG)>25 mg/dl.

If there is a valid calculation, i.e. at least two fasting measurement values in the second group and at least 5 fasting measurement values in the first group of measurement values, in all other cases the fasting trend steady arrow 201 is displayed by the trend indicator 164 at the display 162.

The fasting trend arrows showing in upward, downward or horizontal direction are easy to understand for the patient and provide a reliable and descriptive assessment of the fasting blood glucose value development over a time range of about 1.5 weeks.

In an example embodiment, device 100 may be realized as a two-part device, wherein the data storage 130, the receiving unit 120, the processor 140, the user input unit 150, the display unit 160 with the trend indicator 164, the interface unit 170, and the clock unit 180 are realized as a software program (application or "app") to run on the hardware of a smartphone. The keys 151, 152, 153 and 154 are realized in this case as button fields on the display of a touchscreen.

FIG. 8 shows a case 500 for a medical device in an open state comprising the medical device 100, a box 502 with test strips and a lancet 504. In the example embodiment of FIG. 8, the case 500 is made of a textile material. In an alternative embodiment, the case may be made of a plastic material, a leather material, a combination of any of these materials, and/or the like. The medical device 100, the box 502 and the lancet 504 are fixed to left side the case 500 by means of flexible straps 505 so that each of these elements may be easily removed from the case 500.

On the left side of the case several flash cards 506 are fixed hingedly by two rings 508 to the case 500. Each ring 508 may be opened so that one card or more cards 506 may be removed from the case 500. Each flash card 506 provides important information to the user/patient like explanations and pictures with regard to the buttons, the display, the symbols of the display and their meaning, or the operation of the medical device 100, for example how to tag a measurement value. The flash card 506 provides such information on the front side, but may also provide information on the back side. In order to access the information printed on the backside of each card 506 it may be hinged down (pivoted around the axis of ring 508) by the patient/user so that the backside information is visible. Therefore, the information on the backside is inversely printed so that it is easily readable when the card is hinged down as it is shown in FIG. 8. For easy orientation each flash card 506 may be marked at a top area with a different color. The ring 508 further has the advantage that the card is still fixed to the case when the patient/user reads the backside so that the card cannot get lost. In the state where all flash cards 506 are pivoted such that they are positioned fully within the case 500 the case may be closed using the zipper 510. In the closed state of the case 500 the interior is well protected against environmental impact.

The invention claimed is:

1. A blood glucose measurement system, comprising:
a slot for receiving blood samples of a user;
a sensor in the slot configured to detect the blood samples of the user;
a display device comprising a user interface;
a clock generator configured to automatically generate an associated time stamp for each of a plurality of blood glucose measurement values, the plurality of blood glucose measurement values being generated in response to a trigger signal from the sensor detecting the blood samples of the user;
a data storage adapted to store:
the plurality of blood glucose measurement values,
for each blood glucose measurement value, an associated tag,
for each blood glucose measurement value, an associated time stamp, and
one or more current time ranges, each of the one or more current time ranges corresponding to a predefined event, wherein each predefined event has a corresponding tag; and
a processor adapted to ensure that correct tags and time stamps are stored with the associated blood glucose measurement values by performing the following operations:
receiving a new blood glucose measurement value with an associated time stamp,
comparing the associated time stamp of the new blood glucose measurement value with the stored one or more current time ranges,
if the associated time stamp is within at least one current time range of the one or more current time ranges:
automatically preselecting the corresponding tag of the predefined event to which the at least one current time range corresponds, and
causing a display, on the display device of the user interface, of one or more first graphical representations prompting a user of the blood glucose measurement system to confirm that the preselected corresponding tag is a correct corresponding tag of the predefined event to which the at least one current time range corresponds;
if the associated time stamp is not within at least one current time range of the one or more current time ranges, or if the preselected tag is not confirmed by the user, causing a display, on the user interface, of one or more second graphical representations prompting the user to select one tag of a plurality of tags, each of the plurality of tags corresponding with a predefined event,
responsive to receiving selection data from the user interface indicating that the user selected one tag of the plurality of tags, receiving, from the data storage, the associated time stamps of a predefined number of consecutive recent blood glucose measurement values tagged with the selected one tag,
calculating a new time range for the one predefined event corresponding with the selected one tag, wherein calculating a new time range is at least partly based on the associated time stamps of the predefined number of consecutive recent blood glucose measurement values and on the associated time stamp of the new blood glucose measurement value, and
storing the new time range as the current time range for the one predefined event corresponding with the selected one tag in the data storage such that the current time range for the predefined event corresponding to the selected one tag is automatically changed to the new time range.

2. The blood glucose measurement system according to claim 1, wherein the processor is further adapted to determine, as a validation criterion, whether the associated time stamps of the predefined number of consecutive recent blood glucose measurement values and the associated time stamp of the new measurement value are outside the current time range for the one predefined event corresponding with the selected one tag in the same direction.

3. The blood glucose measurement system according to claim 1, wherein the predefined number of consecutive blood glucose measurement values is 2 or greater.

4. The blood glucose measurement system according to claim 1, wherein at least one of the one or more current time ranges is defined by a center time and a duration, and calculating a new time range includes calculating a shift of the time range, wherein the shift of the time range is calculated as a shift of the center time corresponding to an average value of the time stamps of the at least one part of the predefined number of consecutive recent blood glucose measurement values, wherein the duration of the time range is not changed.

5. The blood glucose measurement system according to claim 4, wherein the average value is the arithmetic mean value or the median value of a time information of the time stamps without considering the date.

6. The blood glucose measurement system according to claim 1, wherein the predefined events for blood glucose measurement values comprises an event nil and at least one of the group of events consisting of fasting, pre-meal breakfast, post-meal breakfast, pre-meal lunch, post-meal lunch, pre-meal supper, post-meal supper, night time and exercise.

7. A method for operating a blood glucose measurement system, the blood glucose measurement system comprising:
   a slot for receiving blood samples;
   a sensor in the slot configured to detect the blood samples of the user;
   a display device comprising a user interface;
   a clock generator configured to automatically generate an associated time stamp for each of a plurality of blood glucose measurement values, the plurality of blood glucose measurement values being generated in response to a trigger signal from the sensor detecting the blood samples of the user; and
   a data storage adapted to store the plurality of blood glucose measurement values, an associated tag for each blood glucose measurement value, an associated time stamp for each blood glucose measurement value, and one or more current time ranges, each of the one or more current time ranges corresponding to a predefined event, wherein each predefined event has a corresponding tag,
wherein the method comprises the following operations to ensure that correct tags and time stamps are stored with the associated blood glucose measurement values:
   receiving a new blood glucose measurement value with an associated time stamp,
   comparing the associated time stamp of the new blood glucose measurement value with the one or more current time ranges,
   if the associated time stamp of the new blood glucose measurement value is within at least one particular current time range of the one or more current time ranges:
      automatically preselecting the corresponding tag of the predefined event corresponding to the at least one current time range, and
      causing a display, on the user interface, of one or more first graphical representations prompting a user of the blood glucose measurement system to confirm that the preselected corresponding tag is a correct corresponding tag of the predefined event to which the at least one current time range corresponds,
   if the associated time stamp is not within at least one current time range of the one or more current time ranges, or if the preselected tag is not confirmed by the user, causing a display, on the user interface, of one or more second graphical representations prompting the user to select one tag of a plurality of tags, each of the plurality of tags corresponding with a predefined event,
   responsive to receiving selection data from the user interface indicating that the user selected one tag of the plurality of tags receiving, from the data storage, the associated time stamps of a predefined number of consecutive recent blood glucose measurement values tagged with the selected one predefined tag,
   calculating a new time range for the one predefined event corresponding with the selected one tag, wherein calculating a new time range is at least partly based on the associated time stamps of the predefined number of consecutive recent blood glucose measurement values and on the associated time stamp of the new blood glucose measurement value, and
   storing the new time range as the current time range for the one predefined event corresponding with the selected one tag in the data storage such that the current time range for the predefined event corresponding to the selected one tag is automatically changed to the new time range.

8. The method according to claim 7, wherein calculating a new time range is further based on a validation criterion, the validation criterion comprising:
   determining whether the associated time stamps of the predefined number of consecutive recent blood glucose measurement values and the associated time stamp of the new blood glucose measurement value are outside the current time range for the one predefined event corresponding with the selected one tag in the same direction.

9. The method according to claim 7, wherein the predefined number of consecutive measurement values is 2 or greater.

10. The method according to claim 7, wherein at least one of the one or more current time ranges is defined by a center time and a duration, and calculating a new time range includes calculating a shift of the time range, wherein the shift of the time range is calculated as a shift of the center time corresponding to an average value of the time stamps of the at least one part of the predefined number of consecutive recent blood glucose measurement values, wherein the duration of the time range is not changed.

11. The method according to claim 10, wherein the average value is the arithmetic mean value or the median value of the time information of time stamps without considering the date.

12. The method according to claim 7, wherein the predefined events for blood glucose measurement values comprises an event nil and at least one of the following group of events comprising fasting, pre-meal breakfast, post-meal breakfast, pre-meal lunch, post-meal lunch, pre meal supper, post meal supper, night time and exercise.

13. A medical device comprising:
   a slot for receiving blood samples of a user;
   a sensor in the slot configured to detect the blood samples of the user;
   a clock generator configured to automatically generate an associated time stamp for each of a plurality of blood glucose measurement values, the plurality of blood glucose measurement values being generated in response to a trigger signal from the sensor detecting the blood samples of the user;

a display device comprising a user interface;
at least one processor;
a data storage adapted to store the plurality of blood glucose measurement values, an associated tag for each blood glucose measurement value, an associated time stamp for each blood glucose measurement value, and one or more current time ranges, each of the one or more current time ranges corresponding to a predefined event, wherein each predefined event has a corresponding tag; and
a non-transitory computer readable medium comprising instructions, which when executed by the at least one processor, causes the at least one processor to perform the following operations to ensure that correct tags and time stamps are stored with the associated blood glucose measurement values:
  receiving, from the medical device or from the data storage, a new blood glucose measurement value with the associated time stamp,
  comparing the associated time stamp of the new blood glucose measurement value with the one or more current time ranges,
  if the associated time stamp of the new blood glucose measurement value is within at least one current time range of the one or more current time ranges:
    automatically preselecting the corresponding tag of the predefined event corresponding to the at least one current time range, and
    causing a display, on the user interface, of one or more first graphical representations prompting a user of the medical device to confirm that the preselected corresponding tag is a correct corresponding tag of the predefined event to which the at least one current time range corresponds;
  if the associated time stamp is not within at least one current time range of the one or more current time ranges or if the preselected tag is not confirmed by the user, causing a display, on the user interface, of one or more second graphical representations prompting the user of the medical device to select one tag of a plurality of tags, each of the plurality of tags corresponding with a predefined event;
  in response to receiving selection data from the user interface indicating that the user selected one tag of the plurality of tags receive, from the data storage, the associated time stamps of a predefined number of consecutive recent blood glucose measurement values tagged with the selected one tag,
  calculating a new time range for the one predefined event corresponding with the selected one tag, wherein calculating a new time range is at least partly based on the associated time stamps of the predefined number of consecutive recent blood glucose measurement values and on the associated time stamp of the new blood glucose measurement value, and
  storing the new time range as current time range for the one predefined event corresponding with the selected one tag in the data storage such that the current time range for the predefined event corresponding with the selected one tag is automatically changed to the new time range.

14. A blood glucose measurement system comprising:
a medical device comprising:
  a slot for receiving blood samples of a user;
  a sensor in the slot configured to detect the blood samples of the user;
  a clock generator configured to automatically generate an associated time stamp for each of a plurality of blood glucose measurement values, the plurality of blood glucose measurement values being generated in response to a trigger signal from the sensor detecting the blood samples of the user;
  a display device comprising a user interface;
  a data storage adapted to store:
    the plurality of blood glucose measurement values,
    for each blood glucose measurement value, an associated tag,
    for each blood glucose measurement value, an associated time stamp,
    one or more current time ranges, each of the one or more current time ranges corresponding to a predefined event, wherein each predefined event has a corresponding tag,
  a processor adapted to ensure that correct tags and time stamps are stored with the associated blood glucose measurement values by performing the following operations:
    receiving a new blood glucose measurement value with an associated time stamp,
    comparing the associated time stamp of the new blood glucose measurement value with the stored one or more current time ranges,
    if the associated time stamp is within at least one current time range of the one or more current time ranges:
      automatically preselecting the corresponding tag of the predefined event to which the at least one current time range corresponds, and
      causing a display, on the user interface, of one or more first graphical representations prompting a user of the medical device to confirm that the preselected corresponding tag is a correct corresponding tag of the predefined event to which at least one current time range corresponds;
    if the associated time stamp is not within at least one current time range of the one or more current time ranges, or if the preselected tag is not confirmed by the user, causing a display, on the user interface, of one or more second graphical representations prompting the user of the medical device to select one tag of a plurality of tags, each of the plurality of tags corresponding with a predefined event,
    responsive to receiving selection data from the user interface indicating that the user selected one tag of the plurality of tags, receive, from the data storage, the associated time stamps of a predefined number of consecutive recent blood glucose measurement values tagged with the selected one tag,
    calculating a new time range for the one predefined event corresponding with the selected one tag, wherein calculating a new time range is at least partly based on the associated time stamps of the predefined number of consecutive recent blood glucose measurement values and on the associated time stamp of the new blood glucose measurement value, and
    storing the new time range as the current time range for the one predefined event corresponding with the selected one tag in the data storage such that the current time range for the predefined event corresponding with the selected one tag is automatically changed to the new time range; and a case adapted to carry and secure the medical device, wherein the case comprises at least one flash card containing information related to a use of the medical device.

* * * * *